United States Patent [19]
Rusin

[11] Patent Number: 5,283,192
[45] Date of Patent: Feb. 1, 1994

[54] BIOLOGICAL PROCESS FOR ENHANCED MANGANESE AND SILVER RECOVERY FROM REFRACTORY MANGANIFEROUS SILVER ORE

[75] Inventor: Patricia A. Rusin, Tuscon, Ariz.

[73] Assignee: Metallurgical and Biological Extraction Systems, Inc., Tucson, Ariz.

[21] Appl. No.: 987,887

[22] Filed: Dec. 9, 1992

Related U.S. Application Data

[60] Division of Ser. No. 682,491, Apr. 9, 1991, abandoned, which is a continuation-in-part of Ser. No. 660,312, Feb. 22, 1991, abandoned.

[51] Int. Cl.$^5$ .................... C12N 1/20; C12N 1/00
[52] U.S. Cl. ................ 435/252.31; 435/262; 435/832; 75/721
[58] Field of Search ............ 435/252.31, 832, 262; 75/721

[56] References Cited

U.S. PATENT DOCUMENTS

| | | | |
|---|---|---|---|
| 4,740,243 | 4/1988 | Krebs-Yuill et al. | 75/101 |
| 4,752,332 | 6/1988 | Wu et al. | 75/101 |
| 4,765,827 | 8/1988 | Clough et al. | 75/2 |
| 5,055,130 | 10/1991 | Arnold et al. | 435/838 |

OTHER PUBLICATIONS

Trimble et al., Applied Microbiology, 16(5):695-702, (May 1968).
Ghiorse et al., Appl. Envir. Micro, 31(6):977-985, (Jun. 1976).
de Vrind et al., J. Bacter., 167(1):30-34, (Jul. 1986).
Gupta, Asha, and Henry L. Ehrlich (1989) "Selective and non-selective bioleaching of manganese from a manganese-containing silver ore" Journal of Biotechnology 9:287-304.

*Primary Examiner*—Douglas W. Robinson
*Assistant Examiner*—Maria Osoteo
*Attorney, Agent, or Firm*—Saliwanchik & Saliwanchik

[57] ABSTRACT

Disclosed is an efficient biological process for recovering silver and manganese from refractory manganiferous silver ore. The process utilizes manganese reducing Bacillus sp. Specifically exemplified is a novel microbe designated Bacillus MBX 69, or mutants thereof Further, gene(s) encoding the enzyme(s) obtainable from the said bacteria can be used by placing such gene(s) on a suitable vector and transforming a competent host. The transformed host then can be used to recover silver and manganese from refractory manganiferous silver ore.

1 Claim, No Drawings

BIOLOGICAL PROCESS FOR ENHANCED MANGANESE AND SILVER RECOVERY FROM REFRACTORY MANGANIFEROUS SILVER ORE

This is a division of application Ser. No. 07/682,491, filed Apr. 9, 1991, now abandoned, which is a continuation-in-part of pending application Ser. No. 07/660,312, filed on Feb. 22, 1991, now abandoned.

BACKGROUND OF THE INVENTION

The recovery of silver from ore is made more difficult by the presence of manganese and other metals in the ore. Such ore is generally referred to as "refractory ore" since at least 80% of the silver is complexed with manganese. Accordingly, the silver mining industry is constantly attempting to discover and develop processes which can be used to recover the desired silver efficiently from other metal components in mined ore.

Chemical processes for recovery of precious metals are disclosed in U.S. Pat. Nos. 4,740,243, 4,752,332, and 4,765,827. None of these patents disclose processes which come close to the recovery efficiency for silver and manganese achieved with the subject invention process.

Biological recovery of silver and manganese from refractory ore has not been very successful to date. For example, Gupta, A., and H. L. Ehrlich in Jour. of Biotechnology (1989) 9:287-304, used a mold, Penicillium, incubated aerobically, without a chelator with the ore. After 5 weeks incubation, he achieved 23.5% solubfflwtion of Mn and 26.5% solubilization of silver. This result is not considered to be an efficient silver or manganese recovery.

There is no known prior art biological process which provides high enough silver recovery yields to be considered an efficient silver or manganese recovery process.

The biological process of the subject invention is the first known process which yields in excess of 90% silver and manganese recovery from refractory manganiferous silver ore. Thus, the subject process can be termed a landmark achievement in the art of mining manganese and silver.

BRIEF SUMMARY OF THE INVENTION

The subject invention concerns the use of novel Bacillus bacteria, which have the property of reducing manganese, to recover silver and manganese from refractory ore, i.e., ore comprising silver, manganese, iron, lead, zinc, and the like. Exemplifying the invention is the use of a novel bacterium, named Bacillus MBX 69, or mutants thereof, in a process to efficiently recover manganese and silver from refractory manganiferous silver ore. The principal contaminant in mined silver ore is generally manganese.

Silver and manganese recovery yields of greater than 90% have been achieved by use of the subject process.

An embodiment of the subject process is the use of the gene(s) obtainable from the manganese reducing Bacidlus bacteria, e.g., Bacillus MBX 69, in a silver and manganese recovery process. The gene(s) can be inserted into another biological host via a suitable biological vector, e.g., a plasmed. The transformed host can then be used in essentially the same manner as the parent Bacillus bacteria to recover manganese and silver from mining ore or other preparations containing silver and metal contaminants, including manganese.

A further embodiment of the subject invention is the use of the enzyme(s) expressed by the gene(s) obtainable from manganese reducing Bacillus bacteria, e.g., Bacillus NMX 69, or mutants thereof, to treat ore, or preparations containing silver, manganese, and other contaminant metals, to separate the manganese and silver from the contaminant metals.

DETAILED DISCLOSURE OF THE INVENTION

Upon contacting mined manganiferous silver ore with a culture of the novel bacterium of the invention, or mutants thereof, for a sufficient time to solubilize metal contaminants in the ore, separating the bacterial culture (liquid) from the residual ore, there is obtained a liquid portion comprising silver and manganese. The residual ore, containing some silver, is processed in a standard fashion through a cyanidation process, and silver is recovered using standard metallurgical techniques. Manganese is recovered from the liquid portion by standard procedures, e.g., the chelated manganese can be extracted into an organic phase such as kerosene and then precipitated out as manganese carbonate by bubbling carbon dioxide through the kerosene extract. Ion exchange can also be used to strip manganese from the growth medium. Other metals such as lead, iron, and zinc could be recovered from the growth medium using similar methods. Silver can be recovered from the growth medium using standard cyanide extraction, precipitation with zinc, or ion exchange, as described in Mineral Processing Technology, 1988, 4th ed. by B. A. Wills, Pergamon Press, N.Y. Preferably, the invention process is conducted under substantially anaerobic conditions.

Without bacteria, manganese solubilization is <2%, and silver recovery by cyanidation is 8-15%. Following biotreatment with a manganese reducing Bacillus bacteria, e.g., Bacillus MBX 69, manganese solubilization was 99.8% and silver recovery following cyanidation was 92.5%.

Manganese reducing Bacillus sp. can be isolated by the following procedure:

Obtain samples of ore of interest and of sediments or water near ore deposit site. Make dilutions of samples in a standard mineral salts medium comprising $MnO_2$. Incubate tubes at about room temperature and examine for Mn reduction. Isolate Mn reducers on solid agar plates and reconfirm Mn reduction in same medum as used for initial isolation.

Identification Perform gram stain of bacterium. Biochemical tests are done and identification is according to Bergey's Manual of Determinative Bacteriology.

Comparative Mn Reduction Kinetics

Combine growth medium, test bacterium and ore in test tube. Incubate with agitation for 2-7 days at room temperature. Analysis for solubilized Mn is performed with a standard colorimetric method, or standard atomic absorption (AA). After incubation at room temperature, add excess cyanide to tube, agitate for 24-48 hrs and analyze supernatant for solubilized silver. Choose bacterium which solubilizes the most manganese and silver.

The novel Bacillus MBX 69 of the invention is characterized as follows:
Gram positive rod shaped bacterium
motile facultative (grows aerobically and anaerobically)
forms terminal swollen endospores
hydrolyzes starch
grows at pH 6–8
grows at approximately 18°–40° C.
ferments glucose, arabinose, raffinose, xylose, trehalose, maltose, mannitol, and melibiose
forms the enzyme catalase
cannot use citrate as sole carbon source
does not hydrolyze urea
does not produce hydrogen sulfide
forms the enzyme gelatinase A biologically pure culture of Bacillus NMX 69 been deposited in the Agricultural Research Service Patent Culture Collection (NRRL), Northern Regional Research Center, 1815 North University Street, Peoria, Ill. 61604, USA.

| Culture | Repository No. | Deposit date |
| --- | --- | --- |
| *Bacillus* MBX 69 | NRRL B-18768 | February 12, 1991 |

The subject culture has been deposited under conditions that assure that access to the culture will be available during the pendency of this patent application to one determined by the Commissioner of Patents and Trademarks to be entitled thereto under 37 CFR 1.14 and 35 U.S.C. 122. The deposit is available as required by foreign patent laws in countries wherein counterparts of the subject application, or its progeny, are filed. However, it should be understood that the availability of a deposit does not constitute a license to practice the subject invention in derogation of patent rights granted by governmental action.

Further, the subject culture deposit wt be stored and made available to the public in accord with the provisions of the Budapest Treaty for the Deposit of Microorganisms, i.e., it will be stored with all the care necessary to keep it viable and uncontaminated for a period of at least five years after the most recent request for the furnishing of a sample of the deposit, and in any case, for a period of at least thirty (30) years after the date of deposit or for the enforceable life of any patent which may issue disclosing the culture. The depositor acknowledges the duty to replace the deposit should the depository be unable to furnish a sample when requested, due to the condition of the deposit. All restrictions on the availability to the public of the subject culture deposit wt be irrevocably removed upon the granting of a patent disclosing it.

Bacillus MBX 69, or mutants thereof, can be cultured in any standard biological medium which supports its growth. Many such media are available for Bacillus cultures from Difco, Detroit, MI. Generally, such a growth medium wt contain a carbon source, e.g., glucose or starch, nitrogen source, e.g., peptone, phosphorous, sulfur, trace elements, and growth factors. Preferably, the culture medium will contain at least about 0.1 M nitrilotriacetic acid (NTA), or a similar chelator, e.g., ethylenediaminetetraacetic acid (EDTA), salicyhc acid, citric acid, acetic acid, or acetylacetone. Mutants of the novel isolate of the invention can be made by procedures well known in the art. For example, an asporogenous mutant can be obtained through ethyhnethane sulfonate (EMS) mutagenesis of the novel isolate. The mutants can be made using ultraviolet light and nitrosoguanidine by procedures well known in the art.

Enzyme(s) produced by the novel microbe of the invention can be recovered from the culture medium of the microbe. The recovery process can be one in which the microbial cells at harvest are lysed and the enzyme(s) recovered from the culture medium by standard procedures. The resulting enzyme preparation can be used to treat refractory ore to solubilize metal contaminants and recover silver and manganese, as disclosed herein. The treatment of refractory ore with an enzyme preparation, as disclosed above, can be by use of columns and other means well known in the enzyme art. The enzyme preparation so used can be in either a crude or essentially pure form.

Novel recombinant microbes can be made by isolating the gene(s) from Bacillus MBX 69, and transforming suitable hosts with the gene(s). The gene(s) encode enzymes which are capable of solubilizing metal contaminants found in silver ore.

A wide variety of ways are available for introducing a gene into a microorganism host under conditions which allow for stable maintenance and expression of the gene. One can provide for DNA constructs which include the transcriptional and translational regulatory signals for expression of the gene, the gene under their regulatory control and a DNA sequence homologous with a sequence in the host organism, whereby integration will occur, and/or a replication system which is functional in the host, whereby integration or stable maintenance will occur.

Various manipulations may be employed for enhancing the expression of the messenger RNA, particularly by using an active promoter, as well as by employing sequences, which enhance the stability of the messenger RNA. The transcriptional and translational termination region wt involve stop codon(s), a terminator region, and optionally, a polyadenylation signal.

In the direction of transcription, namely in the 5' to 3' direction of the coding or sense sequence, the construct will involve the transcriptional regulatory region, if any, and the promoter, where the regulatory region may be either 5' or 3' of the promoter, the ribosomal binding site, the initiation codon, the structural gene having an open reading frame in phase with the initiation codon, the stop codon(s), the polyadenylation signal sequence, if any, and the terminator region. This sequence as a double strand may be used by itself for transformation of a microorganism host, but will usually be included with a DNA sequence involving a marker, where the second DNA sequence may be joined to the expression construct during introduction of the DNA into the host.

A marker structural gene is used to provide for the selection of the host microbe which has acquired the desired nucleotide sequence (via, for example, transformation, electroporation, conjugation, or phage mediated). The marker wt normally provide for selective advantage, for example, providing for biocide resistance, e.g., resistance to antibiotics or heavy metals; complementation, so as to provide prototropy to an auxotrophic host, or the like. Preferably, complementation is employed, so that the modified host may not only be selected, but may also be competitive in the field. One or more markers may be employed in the development of the constructs, as well as for modifying the host. The organisms may be further modified by providing for a competitive advantage against other wild-type microorganisms in the field. For example, genes expressing metal chelating agents, e.g., siderophores, may be introduced into the host along with the structural gene. In this manner, the enhanced expression of a siderophore may provide for a competitive advantage for the host, so that it may effectively compete with wild-type microorganisms.

Where no functional replication system is present, the construct will also include a sequence of at least 50 basepairs (bp), preferably at least about 100 bp, and usually not more than about 1000 bp of a sequence homologous with a sequence in the host. In this way, the probability of legitimate recombination is enhanced, so that the gene wt be integrated into the host and stably maintained by the host. Desirably, the gene will be in close proximity to the gene providing for complementation as well as the gene providing for the competitive advantage. Therefore, in the event that a gene is lost, the resulting organism will be likely to also lose the complementing gene and/or the gene providing for the competitive advantage, so that it will be unable to compete in the environment with the gene retaining the intact construct.

A large number of transcriptional regulatory regions are available from a wide variety of microorganism hosts, such as bacteria, bacteriophage, cyanobacteria, algae, fungi, and the like. Various transcriptional regulatory regions include the regions associated with the LM gene, lac gene, gal gene, the lambda left and right promoters, the Tac promoter, the naturally-occurring promoters associated with the gene, where functional in the host. The termination region may be the termination region normally associated with the transcriptional initiation region or a different transcriptional initiation region, so long as the two regions are compatible and functional in the host.

Where stable episomal maintenance or integration is desired, a plasmed will be employed which has a replication system which is functional in the host. The replication system may be derived from the chromosome, an episomal element normally present in the host or a different host, or a replication system from a virus which is stable in the host.

The gene can be introduced between the transcriptional and translational initiation region and the transcriptional and translational termination region, so as to be under the regulatory control of the initiation region. This construct win be included in a plasmed, which will include at least one replication system, but may include more than one, where one replication system is employed for cloning during the development of the plasmed and the second replication system is necessary for functioning in the ultimate host. In addition, one or more markers may be present, which have been described previously. Where integration is desired, the plasmid will desirably include a sequence homologous with the host genome.

The transformants can be isolated in accordance with conventional ways, usually employing a selection technique, which allows for selection of the desired organism as against unmodified organisms or transferring organisms, when present. The transformants then can be tested for solubilizing contaminant metals found in silver ore.

Suitable host cells can be Gram-negative bacteria, including Enterobacteriaceae, such as Escherichia, and Pseudomonadaceae, such as Pseudomonas.

The recombinant cellular host containing the gene(s) may be grown in any convenient nutrient medium, where the DNA construct provides a selective advantage, providing for a selective medium so that substantially all or all of the cells retain the gene. These cells may then be harvested in accordance with conventional ways.

Following are examples which illustrate procedures, including the best mode, for practicing the invention. These examples should not be construed as limiting. All percentages are by weight and all solvent mixture proportions are by volume unless otherwise noted.

EXAMPLE 1

Culturing Bacillus MBX 69, NRRL B-18768

A subculture of Bacillus MBX 69, NRRL B-18768 can be used to inoculate the following medium, a peptone, glucose, salts medium.

| | |
|---|---|
| Bacto Peptone | 7.5 g/l |
| Glucose | 1.0 g/l |
| $KH_2PO_4$ | 3.4 g/l |
| $K_2HPO_4$ | 4.35 g/l |
| Nitrilotriacetic acid | 0.1 M |
| Salt Solution | 5.0 ml/l |
| $CaCl_2$ Solution | 5.0 ml/l |
| Salts Solution (100 ml) | |
| $MgSO_4.7H_2O$ | 2.46 g |
| $MnSO_4.H_2O$ | 0.04 g |
| $ZnSO_4.7H_2O$ | 0.28 g |
| $FeSO_4.7H_2O$ | 0.40 g |
| $CaCl_2$ Solution (100 ml) | |
| $CaCl_2.2H_2O$ | 3.66 g |
| pH 7.2 | |

The salts solution and $CaCl_2$ solution are filter-sterilized and added to the autoclaved and cooked broth at the time of inoculation. Flasks are incubated at 30° C. on a rotary shaker at 200 rpm for 64 hr.

An alternative growth medium is potato extract, e.g., potato extracted by heat or enzymatically by standard procedures, supplemented with a chelator, e.g., nitrilotriacetic acid, and the like.

The above media and procedures can be used with other manganese reducing Bacillus sp., and can be readily scaled up to large fermentors by procedures well known in the art.

EXAMPLE 2

Biotreatment of Mined Silver Ore

Mined silver ore and bacterial culture of a manganese reducing Bacillus sp., e.g., Bacillus NMX 69, are combined in a bioreactor. The bacteria-ore mixture is incubated at a temperature of about 27° C. with agitation while slowly percolating with nitrogen gas if necessary to maintain anaerobic conditions. Retention time in the bioreactor wt vary with the ore used from about 2 to about 6 days. With some ore samples, the bacterial culture wt need to be replaced with a 50-100% turnover daily. The liquid bacterial culture then can be separated from the residual ore by standard procedures. Soluble silver, manganese and other metals can be chemically stripped from the liquid portion by standard procedures. The residual ore is subject to a standard cyanidation process, and residual silver is recovered through standard metallurgical techniques.

Alternatively, the desired metals can be recovered from the residue and/or liquid portion of a culture or enzyme reaction without first separating the components.

EXAMPLE 3

Cloning of Manganese Reducing Bacillus sp., e.g., MBX 69 Gene(s) Into Baculoviruses The novel gene(s) of the invention can be cloned into baculoviruses such as *Autographa californica* nuclear polyhedrosis virus (AcNPV). Plasmeds can be constructed that contain the ACNPV genome cloned into a commercial cloning vector such as pUC8. The ACNPV genome is modified so that the coding region of the polyhedrin gene is removed and a unique cloning site for a passenger gene is placed directly behind the polyhedrin promoter. Examples of such vectors are pGP-B6874, described by Pennock et al. (Pennock, G. D., Shoemaker, C. and Miler, L. K. [1984] Mol. Ceil. Biol. 4:399–406), and pAC380, described by Smith et al. (Smith, G. E., Summers, M. D. and Fraser, M. J. [1983] Mol Ceil. Biol. 3:2156–2165). The gene(s) coding for the enzyme(s) which solubilize contaminant metals in silver ore can be modified with BamHI linkers at appropriate regions both upstream and downstream from the coding region and inserted into the passenger site of one of the ACNPV vectors.

I claim:

1. A biologically pure culture of Bacillus circulans MBX 69, having all the identifying characteristics of NRRL B-18768, or mutants thereof, having the ability to reduce manganese.

* * * * *

UNITED STATES PATENT AND TRADEMARK OFFICE
CERTIFICATE OF CORRECTION

PATENT NO.     :     5,283,192
DATED          :     February 1, 1994
INVENTOR(S)    :     Patricia A. Rusin It is certified that error appears in the above-identified patent and that said Letters Patent is hereby corrected as shown below:

Column 6   line 54: Delete "bioreactor wt vary" and insert --bioreactor will vary--.

Column 6   line 56: Delete "wt need" and insert --will need--.

Column 7   line 7: Delete "plasmeds" and insert --plasmids--.

Column 7   lines 8-9: Delete "ACNPV" and insert --AcNPV--.

Column 7   line 15: Delete "Miler, L.K." and insert --Miller, L.K.--.

Column 7   line 15: Delete "Mol. Ceil." and insert --Mol. Cell.--.

Column 8   line 3: Delete "Mol. Ceil." and insert --Mol. Cell.--.

Column 8   line 9: Delete "ACNPV" and insert --AcNPV--.

UNITED STATES PATENT AND TRADEMARK OFFICE
CERTIFICATE OF CORRECTION

PATENT NO. : 5,283,192

DATED : February 1, 1994

INVENTOR(S) : Patricia A. Rusin

It is certified that error appears in the above-identified patent and that said Letters Patent is hereby corrected as shown below:

Abstract [57], line 5: Delete "thereol" and insert --thereof--.

Column 1  line 31: Delete "solubfflwtion" and insert --solubilization--.

Column 1  line 61: Delete "Bacidlus" and insert --*Bacillus*--.

Column 1  line 64: Delete "plasmed" and insert --plasmid--.

Column 3  line 13: Delete "NMX 69" and insert --MBX 69--.

Column 3  line 35: Delete "deposit wt be" and insert --deposit will be--.

Column 3  line 49: Delete "deposit wt be" and insert --deposit will be--.

Column 3  line 55: Delete "medium wt contain" and insert --medium will contain--

Column 3  line 61: Delete "salicyhc acid" and insert --salicylic acid--.

UNITED STATES PATENT AND TRADEMARK OFFICE
CERTIFICATE OF CORRECTION

Page 3 of 4

PATENT NO.    :    5,283,192

DATED    :    February 1, 1994

INVENTOR(S)    :    Patricia A. Rusin

It is certified that error appears in the above-identified patent and that said Letters Patent is hereby corrected as shown below:

Column 3    line 65:    Delete "ethyhnethane" and insert --ethylmethane--.

Column 4    line 35:    Delete "region wt involve" and insert --region will involve--.

Column 4    line 56:    Delete "marker wt" and insert --marker will--.

Column 5    line 12:    Delete "gene wt" and insert --gene will--.

Column 5    line 27:    Delete "LM gene" and insert --trp gene--.

Column 5    line 36:    Delete "plasmed" and insert --plasmid--.

Column 5    line 46:    Delete "construct win be" and insert --construct will be--.

Column 5    line 46:    Delete "plasmed" and insert --plasmid--.

Column 5    line 50:    Delete "plasmed" and insert --plasmid--.

Column 6    line 49:    Delete "NMX 69" and insert --MBX 69--.

UNITED STATES PATENT AND TRADEMARK OFFICE
CERTIFICATE OF CORRECTION

PATENT NO. : 5,283,192
DATED : February 1, 1994
INVENTOR(S) : Patricia A. Rusin

It is certified that error appears in the above-indentified patent and that said Letters Patent is hereby corrected as shown below:

Column 8    line 9:   Delete "ACNPV" and insert --AcNPV--.

Signed and Sealed this

Fourteenth Day of February, 1995

Attest:

BRUCE LEHMAN

Attesting Officer    Commissioner of Patents and Trademarks